United States Patent
Gao et al.

(10) Patent No.: US 9,080,152 B2
(45) Date of Patent: Jul. 14, 2015

(54) METHODS FOR PROLIFERATION OF ANTIGEN-SPECIFIC T CELLS

(75) Inventors: Bin Gao, Beijing (CN); Jie Ding, Beijing (CN)

(73) Assignee: Nantong Biotechnology Park Development and Investment Co., Ltd., Nantong (CN)

( * ) Notice: Subject to any disclaimer, the term of this patent is extended or adjusted under 35 U.S.C. 154(b) by 636 days.

(21) Appl. No.: 13/254,039

(22) PCT Filed: Apr. 30, 2009

(86) PCT No.: PCT/CN2009/000481
§ 371 (c)(1),
(2), (4) Date: Jan. 5, 2012

(87) PCT Pub. No.: WO2010/099637
PCT Pub. Date: Sep. 10, 2010

(65) Prior Publication Data
US 2012/0100180 A1    Apr. 26, 2012

(30) Foreign Application Priority Data
Mar. 5, 2009  (CN) .......................... 2009 1 0079259

(51) Int. Cl.
| A61K 39/12 | (2006.01) |
| A61K 39/02 | (2006.01) |
| A61K 45/06 | (2006.01) |
| C12N 5/0783 | (2010.01) |
| A61K 35/12 | (2015.01) |

(52) U.S. Cl.
CPC ......... *C12N 5/0636* (2013.01); *A61K 2035/124* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| 2003/0148982 A1* | 8/2003 | Brenner et al. ................. 514/44 |
| 2005/0009180 A1* | 1/2005 | Yang et al. .................... 435/455 |
| 2006/0269973 A1 | 11/2006 | Yee .............................. 435/7.23 |

FOREIGN PATENT DOCUMENTS

CN    101273122    9/2008

OTHER PUBLICATIONS

Fu et al. (Journal of Immunological Methods, 2008, vol. 335, p. 90-97 in IDS on Oct. 25, 2011).* de Wit et al., "Efficient generation and growth of influenza virus A/PR/8/34 from eight cDNA fragments," *Virus Research* 103:155-161, 2004.
Estcourt et al., "Altered primary CD8+ T cell response to a modified virus Ankara(MVA)-vectored vaccine in the absence of CD4+ T cell help," *Eur. J. Immunol.* 35:3460-3467, 2005.
Fu et al., "Investigation of endogenous antigen processing by delivery of an intact protein into cells," *Journal of Immunological Methods* 335:90-97, 2008.
Korn et al., "Bispecific Single-Chain Diabody-Mediated Killing of Endoglin-Positive Endothelial Cells by Cytotoxic T Lymphocytes," *J. Immunother.* 27(2):99-106, 2004.
Lamers et al., "Phoenix-ampho outperforms PG13 as retroviral packaging cells to transduce human T cells with tumor-specific receptors: implications for clinical immunogene therapy of cancer," *Cancer Gene Therapy* 13:503-509, 2006.
Lamers et al., "Process validation and clinical evaluation of a protocol to generate gene-modified T lymphocytes for imunogene therapy for metastatic renal cell carcinoma: GMP-controlled transduction and expansion of patient's T lymphocytes using a carboxy anhydrase IX-specific scFv transgene," *Cytotherapy* 8(6):542-553, 2006.
Morgan et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *The Journal of Immunology* 171:3287-3295, 2003.
Mullins et al., "Route of Immunization with Peptide-pulsed Dendritic Cells Controls the Distribution of Memory and Effector T Cells in Lymphoid Tissues and Determines the Pattern of Regional Tumor Control," *J. Exp. Med.* 198(7):1023-1034, 2003.
Patel et al., "T-cell killing of heterogenous tumor or viral targets with bispecific chimeric immune receptors," *Cancer Gene Therapy* 7(8):1127-1134, 2000.
Quan et al., "Regulation of human heme oxygenase in endothelial cells by using sense and antisense retroviral constructs," *PNAS* 98(21):12203-12208, 2001.
Wang et al., "T cells that express chimeric antigen receptor: A new anti-cancer treatment strategy,", *Chinese Journal of Immunology* 17:624-627, 2001 (w/English abstract).
Zhou et al., "Screening and Identification of Severe Acute Respiratory Syndrome-Associated Coronavirus-Specific CTL Epitopes," *The Journal of Immunology* 177:2138-2145, 2006.

* cited by examiner

*Primary Examiner* — Agnieszka Boesen
(74) *Attorney, Agent, or Firm* — Seed IP Law Group PLLC

(57) ABSTRACT

Methods for expansion of antigen-specific T cells are provided. Said methods include following steps: generating antigen-specific T cells by stimulation of T cells with antigen A; introducing genes encoding immune recognition molecule specific to major histocompatibility complex (MHC) molecule bound with a peptide derived from antigen B into the antigen A specific T cell to produce bi-specific T cells recognizing both target cells expressing antigen A peptide associated MHC and target cells expressing antigen B peptide associated MHC; stimulating the bi-specific T cells by antigen A for expansion of the bi-specific T cells in vitro or in vivo. Methods of the present invention can be applied to expand various of T cells with specific to cancer cells with tumor antigen peptide loaded MHC molecules for adoptive therapy against unmet medical need such as tumors etc.

10 Claims, 8 Drawing Sheets

SEQUENCE LISTING

```
<160> NUMBER OF SEQ ID NOS: 2

<210> SEQ ID NO 1
<211> LENGTH: 1149
<212> TYPE: DNA
<213> ORGANISM: Homo sapiens

<400> SEQUENCE: 1
atggtgaaga tccggcaatt tttgttggct attttgtggc ttcagctaag ctgtgtaagt      60
gccgccaaaa atgaagtgga gcagagtcct cagaacctga ctgcccagga aggagaattt     120
atcacaatca actgcagtta ctcggtagga ataagtgcct tacactggct gcaacagcat     180
ccaggaggag gcattgtttc cttgtttatg ctgagctcag ggaagaagaa gcatggaaga     240
```

```
ttaattgcca caataaacat acaggaaaag cacagctccc tgcacatcac agcctcccat    300
cccagagact ctgccgtcta catctgtgct gcctcattaa ttcagggagc ccagaagctg    360
gtatttggcc aaggaaccag gctgactatc aacccaaata tccagaaccc tgaccctgcc    420
gtgtaccagc tgagagactc taaatccagt gacaagtctg tctgcctatt caccgatttt    480
gattctcaaa caaatgtgtc acaaagtaag gattctgatg tgtatatcac agacaaaact    540
gtgctagaca tgaggtctat ggacttcaag agcaacagtg ctgtggcctg gagcaacaaa    600
tctgactttg catgtgcaaa cgccttcaac aacagcatta ttccagaaga caccttcttc    660
cccagcccag aaagttcctg tgatgtcaag ctggtcgaga aaagctttga aacagatacg    720
aacctaaact ttcaaaacct gtcagtgatt gggttccgaa tcctcctcct gaaagtggcc    780
gggtttaatc tgctcatgac gctgcggctg tggtccagct gagacctgca agattgtaag    840
acagcctgtg ctccctcgct ccttcctctg cattgcccct cttctccctc tccaaacaga    900
gggaactctc ccaccccccaa ggaggtgaaa gctgctacca cctctgtgcc ccccggcaa    960 tgccaccaac tggatcctac ccgaatttat gattaagatt gctgagagct gccaaacact   1020
gctgctaccc cctctgttcc cttattgctg cttgtcactg cctgacaatt cacgggcgga   1080
ggcataccta cgagctaagt gggattcctc tcaggggctg tcaggaattc ccaccggtgg   1140
gtctaaggt                                                           1149

<210> SEQ ID NO 2
<211> LENGTH: 1163
<212> TYPE: DNA
<213> ORGANISM: Homo sapiens

<400> SEQUENCE: 2
gccatggact cctggacctt ctgctgtgtg tcccttttgca tcctggtagc gaagcataca     60
gatgctggag ttatccagtc accccgccat gaggtgacag agatgggaca agaagtgact    120
ctgagatgta acccaatttc aggccacaac tcccttttct ggtacagaca gaccatgatg    180
cggggactgg agttgctcat ttactttaac aacaacgttc cgatagatga ttcagggatg    240
cccgaggatc gattctcagc taagatgcct aatgcatcat tctccactct gaagatccag    300
ccctcagaac ccaggggactc agctgtgtac ttctgtgcca gcagcccggg ggcaatgag    360 cagttcttcg gccagggac acggctcacc gtgctagagg acctgaaaaa cgtgttccca    420
cccgaggtcg ctgtgtttga gccatcagaa gcagagatct cccacaccca aaaggccaca    480
ctggtatgcc tggccacagg cttctacccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660 aaccccgca accacttccg ctgtcaagtc cagttctacg gctctcgga gaatgacgag    720 tggacccagg ataggggccaa acctgtcacc cagatcgtca gcgccgaggc ctggggtaga   780
gcagactgtg gcttcacctc cgagtcttac cagcaagggg tcctgtctgc caccatcctc    840
tatgagatct tgctagggaa ggccaccttg tatgccgtgc tggtcagtgc cctcgtgctg    900
atggccatgg tcaagagaaa ggattccaga gctagctcca aaccatccag tcgacgatcc    960
ctcgagagct ggcccatcga taaaataaag attttatttta gtctcagaag aaggggatga   1020
cgacccagct gtagtttgca gctagctagt tacgcatttg caaggcatga aaaatactta   1080
```

```
cctgaataga gagtcgatca gtcagaccga tgaacgctga attggaccac aggattcgtg    1140
gtagacagtt ctggccggct cag                                            1163
```

METHODS FOR PROLIFERATION OF ANTIGEN-SPECIFIC T CELLS

STATEMENT REGARDING SEQUENCE LISTING

Figure 1:
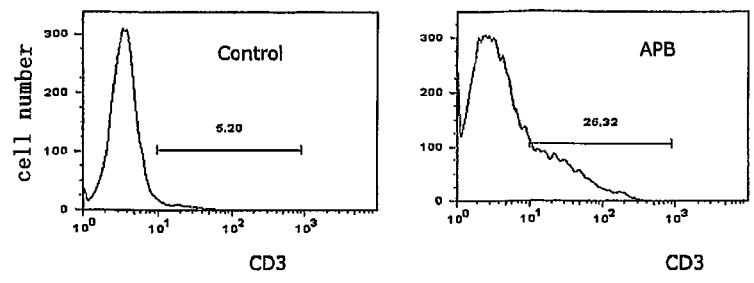
Figure 1:
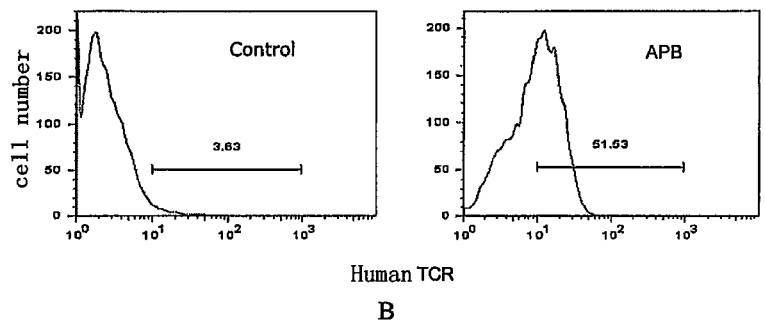
Figure 1:
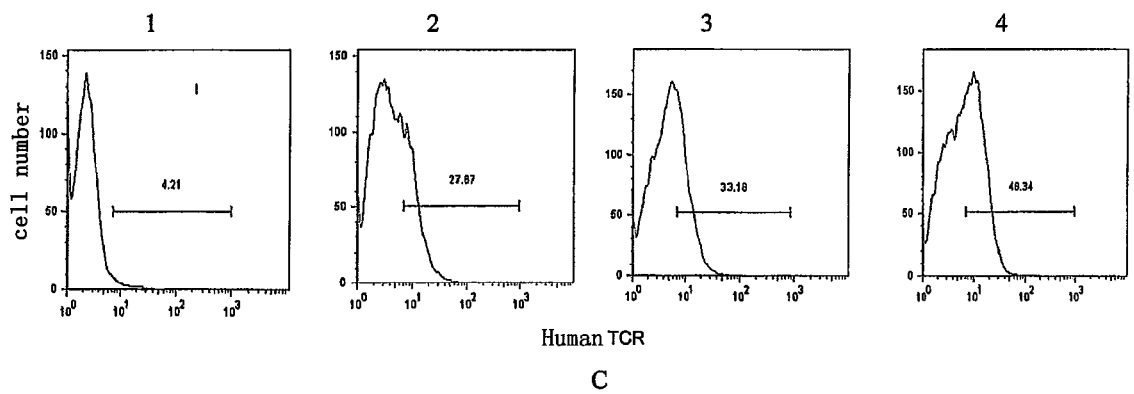

The Sequence Listing associated with this application is provided in text format in lieu of a paper copy, and is hereby incorporated by reference into the specification. The name of the text file containing the Sequence Listing is 480294_401USPC_SEQUENCE_LISTING.txt. The text file is 7 KB, was created on Nov. 29, 2011, and is being submitted electronically via EFS-Web.

TECHNICAL FIELD

The invention mainly involves a method expansion of antigen-specific T-cell

EXISTING TECHNOLOGIES

Cellular immunotherapy has been gradually applied in the treatment of cancer and tumor with some promising results emerged. However, the difficulty to produce large quantity of T cells for the therapy is a major obstacle for the further development of this promising therapy. Currently, the expansion of T cells is carried out by the stimulation of cultured T cells with antibody combined with cytokines, for example: T cells are usually expanded with anti-CD3 antibody plus interleukin-2. However, this method has some disadvantages with non-specific proliferation and insufficient production of T cells. Another method for T cell expansion is the proliferation of T cells stimulated by antigen-presenting cells (such as dendritic cells, B cells, etc.). But to obtain enough antigen-presenting cells itself is a time-consuming task, which could not meet the clinical requirements. Therefore, an effective method for the expansion of a large number of antigen-specific T cells is in urgent need.

DETAILS OF THE INVENTION

One objective of this invention is to provide a method for the expansion of antigen-specific T-cells.

The present invention provides a method for the expansion of antigen-specific T-cell, including the following steps: stimulate T cells with original antigen A to obtain antigen A-specific T cells with surface molecules recognizing pMHC (major histocompatibility complex molecules associated with a peptide derived from antigen A); transfer the genes encoding immune recognition molecules for antigen B peptide associated MHC molecule into the aforementioned immunogen A-specific T-cells, and obtain the double-specific T-cells with antigen-B derived peptide MHC-specific as well as antigen A derived peptide associated MHC molecules. Finally, expand the double-specific T-cells with antigen A.

The aforementioned antigen A refers to a virus, a bacteria, and a chimeric protein, or allogeneic antigen or a peptide with more than 7 and less than 35 amino acids, where a virus refers to the virus with strong immunogenicity and clearly-identified immune response mechanism, and an ability to rapidly and effectively stimulate immune response in immune cells and induce the proliferation of immune cells without causing pathogenicity in mammalian cells, such as influenza virus, EB virus, CMV, etc.

The aforementioned immune recognition molecules that recognize antigen-B peptide-MHC molecule complex include T-cell receptor (TCR), T cell receptor (TCR)-like antibodies, killing cell activated receptors (KAR) and killing inhibitory receptors (KIR) on the NK cell surface.

Another purpose of the invention is to provide a method to make bi-specific antigen-specific T cells.

The invention provides method for making bi-specific antigen-specific T cells, in accordance with the method of preparation includes the following steps to get: introducing encoding gene of immune recognition molecule for antigen B peptide associated MHC (pMHC) into antigen A pMHC specific T cell; generating the bi-specific T cells recognizing both target cells expressing antigen A pMHC and target cells expressing antigen B pMHC.

The aforementioned antigen A refers to virus, bacteria, and peptide with more than 7 and less than 35 amino acids, chimeric protein, allogeneic antigens, where the virus refers to the virus with strong immunogenicity without causing serious pathogenicity in mammalian cells, such as influenza virus, EB virus, CMV, etc.

The aforementioned immune recognition molecules that recognize antigen-B peptide-MHC complex include T-cell receptor, T cell receptor (TCR)-like antibodies, killing cell activated receptors and killing inhibitory receptors on the NK cell surface.

The above-mentioned method can be characterized as immunogenic peptide-MHC complex specific T cells are obtained by immunizing a living subject with antigen A.

The method described for the proliferation of T cells using the following protocols described in 1), 2) or 3):

1) to stimulate the proliferation of the methods described include the following steps: Antigen B specific T-cells are obtained as described by immunizing a living subject with the antigen A, and antigen B specific T cells are amplified by repeated stimulation of antigen A in vivo.

2) to stimulate the proliferation of the methods described include the following steps: co-culture the aforementioned antigen B specific T cells with antigen A, and the proliferation of the antigen B specific T cells are obtained by stimulation of antigen A in vitro cell culture.

3) to stimulate the proliferation of the methods described include the following steps: co-culture the aforementioned antigen B specific T cells and the feeder cells expressing antigen A, and the antigen B specific T cells are amplified through stimulation by antigen A in vitro cell culture.

Transfer method is described as transduction or transfection by the virus vector, liposomes, cationic polymers, or electroporation; viral vector as described is a retroviral vector, a lentiviral vector or an adeno-associated virus vector.

The transduction method described are as follows 1), 2), 3) or 4):

1) Co-culture the Packaging cells that produce the recombinant virus, with antigen A specific T cells and antigen A.

2) Co-culture the Packaging cells that package the recombinant virus with antigen A specific T cells and the feeder cells expressing MHC associated with a peptide derived from antigen A;

3) Co-culture the recombinant virus, antigen A specific T cells and antigen A;

4) Co-culture the recombinant virus, antigen A specific T cells and the feeder cells expressing MHC associated a peptide from antigen A;

Recombinant virus containing the above mentioned encoding genes of immune recognition molecules for antigen B peptide-MHC complex.

The methods and cells as described Antigen B is a tumor differentiation antigen. The tumor mentioned is melanoma. Antigen B can be described as melanoma differentiation antigen gp100.

The mentioned immune recognition molecule specific to antigen B peptide-MHC complex is described as melanoma differentiation antigen gp100 specific T cell receptor proteins.

Described anti-melanoma differentiation antigen gp100 specific T cell receptor proteins-encoding genes including the fragment 1 and fragment 2, the nucleotide sequence of fragment 1 is shown in the sequence table as the sequence 1, the nucleotide sequence of fragment 2 is shown in the sequence table as the sequence 2.

Any of the aforementioned combined antigen A is prepared with the feeder cells in accordance with the following step: Firstly, co-culture the aforementioned antigen-A and feeder cells; finally, obtain the feeder cells combined with antigen A after the treatment of cells with mitomycin.

Any of the above described antigen-specific T cells in the treatment of diseases also belong to the scope of protection of this invention. Wherein the treatment mentioned is specifically for cell based adoptive therapy.

The principle of the invention is to obtain the specific T-cells targeted at antigen-A peptide-MHC molecule (major histocompatibility complex); transfer the encoding genes of immune recognition molecules of peptide-MHC molecule complex that can recognize the target antigen B p-MHC into antigen A-specific T-cells to obtain the double-specific T-cells against both antigen A pMHC molecules and antigen B pMHC; and these T-cells are amplified with repeat stimulation by antigen A.

The invention is suitable for the proliferation of specific T-cells of the antigens with strong or weak immunogenicity, especially for the antigens with the weak-immunogenicity such as certain tumor antigens, for example: melanoma antigen.

In the present invention, the obtained double-specific T-cells, into which the immune recognition molecules of antigen-B specific peptide-MHC molecules complex are transferred, are mainly proliferated through the stimulation of antigen A with stronger immunogenicity. It overcomes the limitation that the antigen with weak immunogenicity could not induce proliferation of its specific T-cells in vitro, and demonstrates a good proliferation, and the proliferated immune cells have a higher killing rate for its targeted cells. Furthermore, this method is simple to operate at a relatively low cost. Therefore, the proliferation method is suitable for the preparation of a variety of antigen-specific immune cells at a large quantity for the transfusion immunotherapy in various tumors or other diseases.

ILLUSTRATIONS

FIG. 1: Production of recombinant retroviruses carrying immune molecule for the recognition of pMHC on target cells with a packaging cell line.

Figure 2:
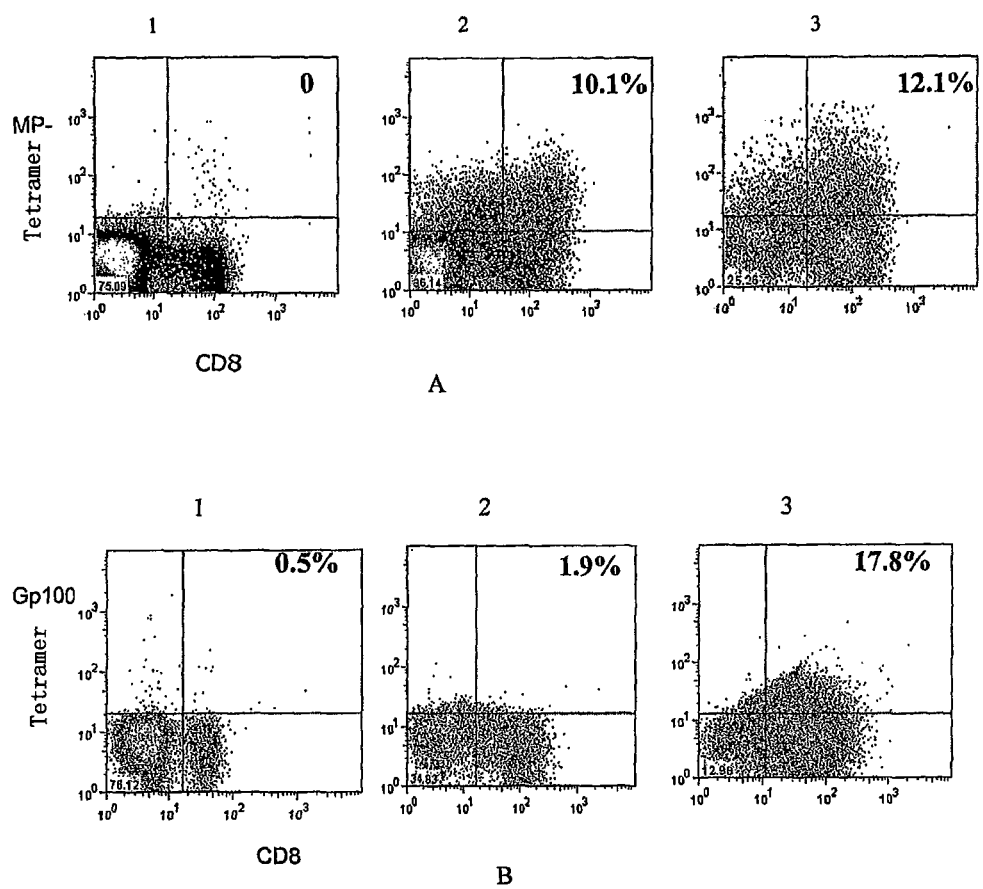

FIG. 2: Staining results of double-specific T-cells against both gp100 peptide or MP peptide pMHC with tetramers in influenza virus FIG. 3: Staining results of double-specific T-cells against both gp100 peptide pMHC or MP peptide pMHC in intracellular cytokine staining assays.

Figure 4:
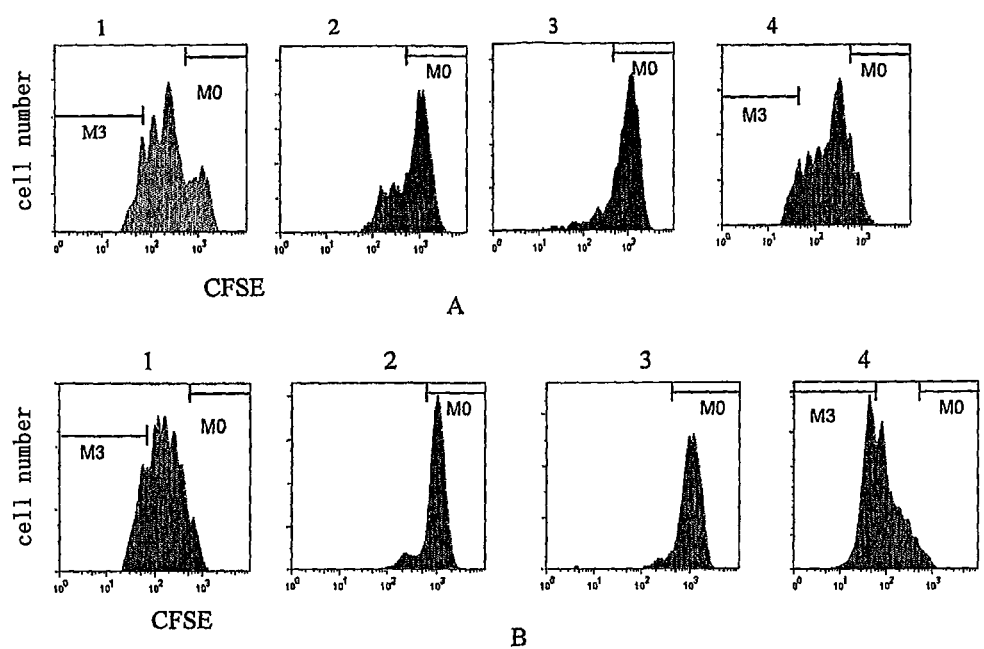
Figure 5:
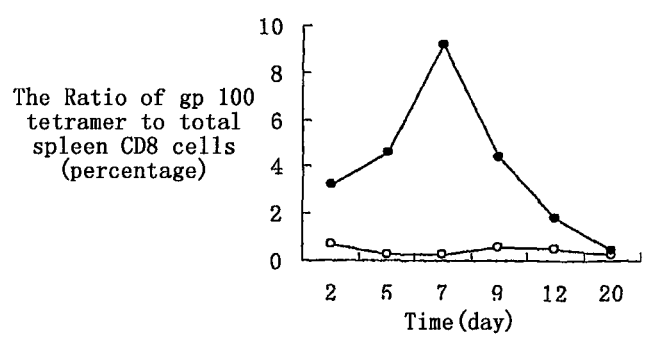
Figure 6:
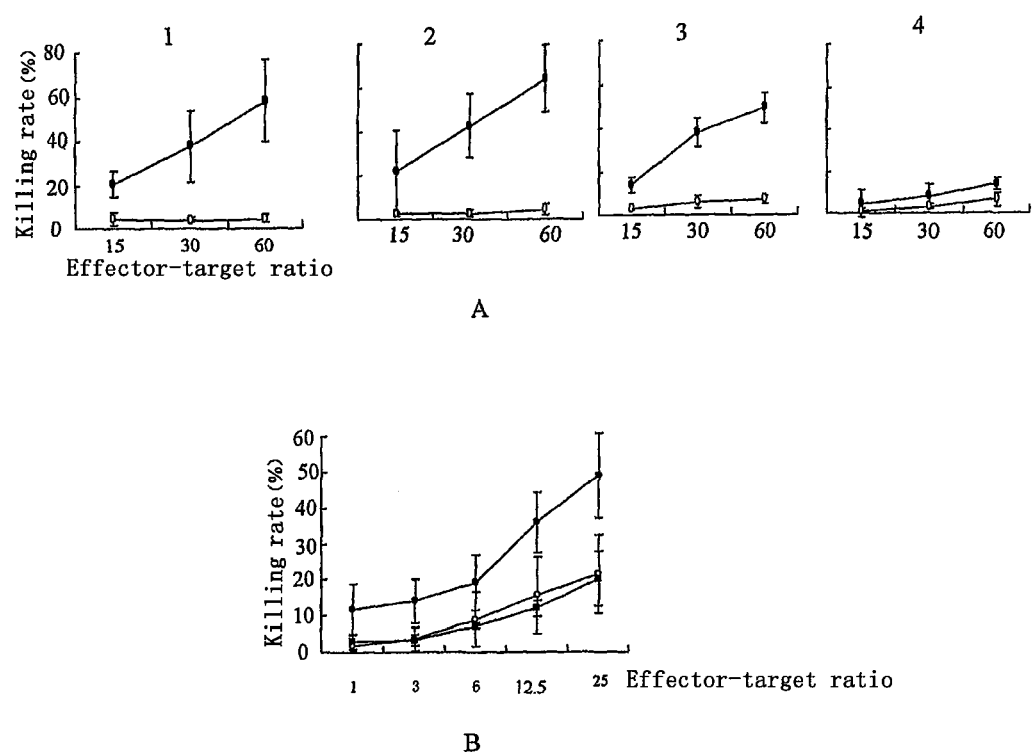

FIG. 4 Proliferation after the in vitro co-culture of double-specific T-cells with different stimuli FIG. 5 In vivo Proliferation of the double-specific T-cells in HLA-A2/Kb transgenic mice FIG. 6 In vitro killing target cells and tumor by the double-specific T-cells.

Figure 7:
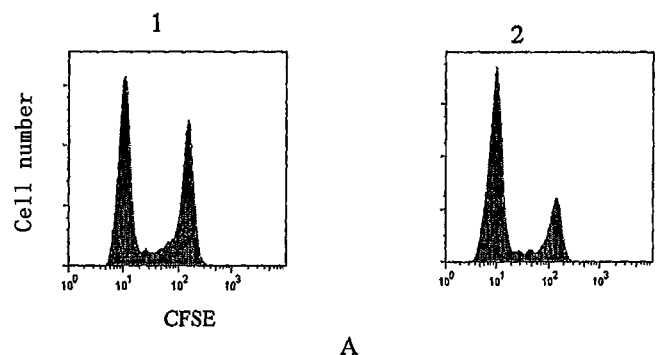
Figure 7:
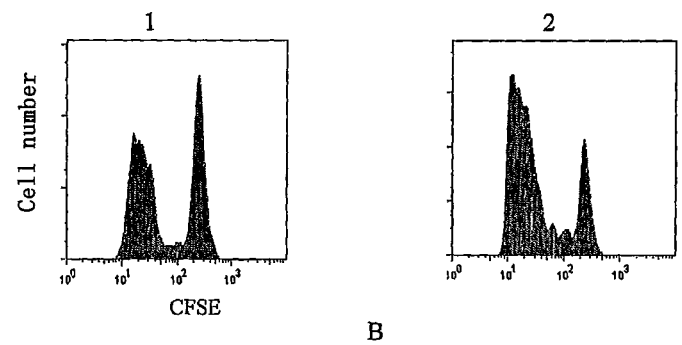
Figure 7:
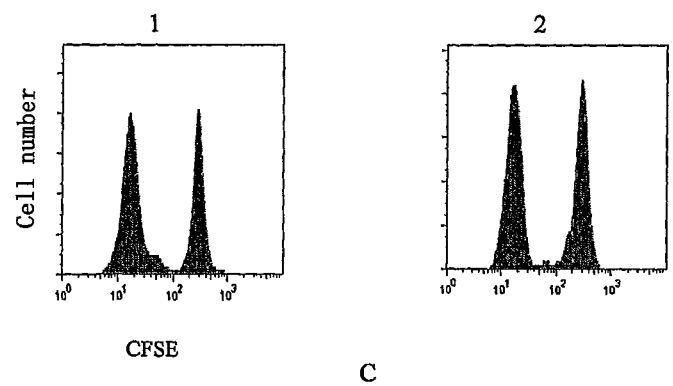

FIG. 7 In vivo killing target cells associated with tumor antigens in HLA-A2/Kb transgenic mice by the double-specific T-cells.

Figure 8:
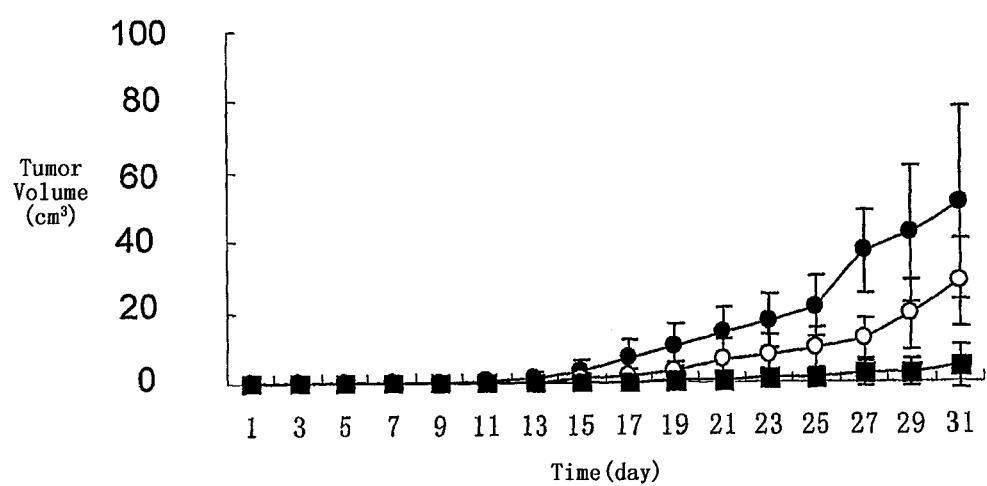

FIG. 8 In vivo melanoma suppression results of the double-specific T-cells in naked mice.

IMPLEMENTATION DETAILS

The experimental methods in the following examples, if no special statement, refer to the conventional methods.

The materials and reagents in the following examples, if no special statement, can be purchased from a commercial company Phoenix-Eco retroviral packaging cells (Morgan, R. a., et al., High efficiency TCR gene transfer into primary human lymphocytes affords avid recognition of melanoma tumor antigen glycoprotein 100 and does not alter the recognition of autologous melanoma antigens. J Immunol, 2003.171(6):p. 3287-95) (IMCAS).

PT67 retroviral packaging cells (Quan, S., et al. Regulation of human heme oxygenase in endothelial cells by using sense and antisense retroviral constructs. PNAS, 2001. 98(21): p. 12203-08) (IMCAS).

Supt1 human lymphoma cell line (Morgan, R. A., et al., High efficiency TCR gene transfer into primary human lymphocytes affords avid recognition of melanoma tumor antigen glycoprotein 100 and does not alter the recognition of autologous melanoma antigens. J Immunol, 2003.171(6):p. 3287-95) (IMCAS).

APB plasmid (Morgan, R. A., et aL., High efficiency TCR gene transfer into primary human lymphocytes affords avid recognition of melanoma tumor antigen glycoprotein 100 and does not alter the recognition of autologous melanoma antigens. J Immunol, 2003.171(6):p 3287-95) (IMCAS), APB plasmid contains the encoding genes of the anti-melanoma gp100 TCR protein, including fragment 1 and 2; and the nucleotide sequence of the fragment 1 and 2 are indicated in The Tables.

Influenza virus is influenza virus A/PR/8/34 PR/8/34. (de Wit, E., et al., Efficient generation and growth of influenza virus A/PR/8/34 from eight cDNA fragments. Virus Res, 2004.103(1-2):p. 155-61.) (IMCAS).

HLA-A2/Kb transgenic mice (Zhou, M., et al., Screening and identification of severe acute respiratory syndrome-associated coronavirus-specific CTL epitopes. J Immunol, 2006.177(4):p. 2138-45.) (IMCAS)

IL-2, purchased from Chiron B. V., Amsterdam, The Netherlands.

Co-culture medium: RPMI1640 medium, containing 10% (volume percentage content) fetal bovine serum, 2 mM glutamine, 100 U/ml penicillin, 10 ug/ml streptomycin, $5 \times 10^{-2}$ mM 2-mercaptoethanol.

Example 1

Preparation of Double-Specific T Cells (Anti-Tumor Specific and Anti-Influenza Virus-Specific T Cells)

1 Preparation of Packaging Cell Line Expressing Recombinant Virus (Containing the Anti-Melanoma gp100TCR Protein Encoding Genes).

Transfect Phoenix-Eco cells with APB plasmid to prepare the PT67 packaging cells infected with viral supernatant. Infect SupT1 human tumor cell lines respectively with the infected supernatant of monoclonal PT67 cells, determine the human CD3 expression with uninfected SupT1 human tumor cell lines as blank control. The method is used to screen the packaging cell line that could generate the highest possible viral titer.

The test results are shown in FIG. 1A, it indicated that the screened PT67 packaging cell line could generate very high viral titer (that is, it could increase the human CD3 expression on the surface of SupT1 human tumor cell line), therefore it could serve as the recombinant virus-producing packaging cell line in the following experiment.

2 Preparation of Double-Specific T-Cells (1) Immunise mice with Influenza virus—: nasal immunization of HLA-A2/Kb transgenic mice with influenza virus. Influenza virus (2) Preparation of mice spleen lymphocytes: 2-4 weeks after immunization, the spleen cells of mice are taken out first. After grinding, the spleen cell suspension is prepared after twice filtration with 200 mesh sieve, the lysis solution of red blood cells is added to cell suspension, erythrocyte debris and platelets are centrifuged and removed, lymphocytes are collected and washed 3 times with 1640 cell culture medium containing 10% fetal calf serum, and the lymphocytes are suspended with co-culture medium.

(3) Preparation of double-specific T cells: The obtained lymphocytes in Step (2) are inoculated into co-culture medium containing the PT67 packaging cells screened in the step-1 (the number of ratio of PT67 packaging cells and lymphocytes is $8 \times 10^4 : 1 \times 10^6$) and producing retrovirus (human TCR expressing anti-gp100 melanoma gp100), influenza virus (the ratio of influenza virus and T cell is ratio of $2 \times 10^6 EID50 : 1 \times 10^6$), and the mixture is cultivated for 5 days under the conditions of 37° C. and 5% $CO_2$. IL-2 is added into the co-culture system after 24-48 hour cultivation (the final concentration of IL-2 in the system is up to 50 IU/ml), and then IL-2 is renewed every day, to obtain double-specific T cells (anti-melanoma-specific and anti-influenza virus-specific T cells)

Determine anti-gp100-TCR expression on the T cell surface at different time points of co-culture.

Repeat the tests 3 times, and the results were shown in FIGS. 1B and 1C, which demonstrated that the surface expression of human gp100-TCR could be detected with anti-human TCR ($\alpha/\beta$)-FITC (BD Biosciences, PharMingen, CA, USA. Cat.333140), and indicated that the retrovirus (APB) had successfully infected Mice T-cells, achieved double-specific T cells (anti-melanoma-specific and anti-influenza virus-specific T cells).

For further amplification of double-specific T cells, absorb suspension cells, remove dead cells, add the influenza virus to stimulate the feeder cells (mice spleen cells with the same cell line) treated with mitomycin (80 μg/ml, 37 □, 2 h) and 50 IU/ml IL-2, co-culture continuously 3-5 days under the conditions of 37 □ and 5% $CO_2$, and obtain sufficient double-specific T-cells.

(4) Preparation of anti-influenza virus-specific T cells: nasal immunization of HLA-A2/Kb transgenic mice with influenza virus, 2-4 weeks after immunization, take out the spleen lymphocytes of mice, add influenza virus up to the final concentration of $2 \times 10^6 EID50$/ml in the culture system, co-culture for 5-10 days under the conditions of 37 □ and 5% $CO_2$. IL-2 was added into the co-culture system after 24-48 hour cultivation (the final concentration of IL-2 in the system is up to 50 IU/ml), and then IL-2 was added every day to obtain double-specific T cells (anti-melanoma-specific and anti-influenza virus-specific T cells)

FIG. 1A indicated the human CD3 expression on the surface of SupT1 cells after infected with retrovirus produced by packaging cell line PT67. Control indicated SupT1 not infected with retrovirus, while APB indicated SupT1 infected with retrovirus. The X-axis is the relative fluorescence intensity values of human CD3 (human leukocyte differentiation antigen-3) while the Y-axis was the number of cells.

FIG. 1B indicated human TCR (T cell antigen receptor) expression on the surface of mice T-cell infected with retrovirus (APB) and stimulated by influenza virus. X-axis indicated the relative intensity of green fluorescence of human TCR, while the Y-axis indicated the amount of cells.

FIG. 1C indicated human TCR (T cell antigen receptor) expression on the surface of mice T-cell after different times of infection with retrovirus (APB) and stimulation by influenza virus. X-axis indicated the relative intensity of green fluorescence of human TCR, while the Y-axis indicated the number of cells.

Example 2

Double-Specific T Cell Proliferation and Function

The following procedures are conducted to test the double-specific T-cells obtained in Example 1.

Prepare the melanoma antigen gp100 peptide tetramer in accordance with the method described in the relevant documents (Estcourt, M. J., A. J. McMichael, and T. Hanke, Altered primary CD8+T cell response to a modified virus Ankara (MVA)-vectored vaccine in the absence of CD4+T cell help. Eur J Immunol, 2005.35(12):p. 3460-7).

Prepare the MP matrix proteins of influenza virus antigen peptide tetramer in accordance with the method described in the documents (Estcourt, M. J., A. J. McMichael, and T. Hanke, Altered primary CD8+T cell response to a modified virus Ankara (MVA)-vectored vaccine in the absence of CD4+T cell help. Eur J Immunol, 2005.35(12):p. 3460-7).

FITC-labeled anti-mouse CD8: purchased from BD, PharMingen, CA, USA;

Anti-mouse IFN-γ-PE: purchased from eBioscience, Product number 12-7311-71;

Monensin: purchased from eBioscience, Product number 00-4505-51;

Penetration buffer: purchased from eBioscience, Product number 00-8333;

Naïve T cells: HLA-A2 transgenic mouse spleen T cells separated before any immunization, are the naive T cells.

1. Tetramer Staining and Intracellular Cytokine Staining

To conduct the tests with double-specific T-cells, anti-influenza virus-specific T cells, and naive T cells are used as experimental cells. The test method is detailed as follows with the double-specific T-cells as example.

Tetramer staining: wash double-specific T cells twice with PBS, re-suspend them in 100 μlPBS, add MP peptide tetramer (PE) or gp100 peptide tetramer (PE), stain at 37° C. for 20 min, add anti-mouse CD8 monoclonal antibody at room temperature and stain for 20 min, wash twice with PBS and re-suspend them into 500 μl PBS, then transfer them into flow cytometry for counting.

Intracellular cytokine staining: inoculate double-specific T-cells into co-culture medium, add gp100 peptide (whose concentrations in the culture system is 20 μM) and MP influenza virus peptide (whose concentrations in the culture system is 20 μM) into different treatment groups respectively, after 1-2 hour stimulation, add monensin (whose concentrations of gp100 peptide in the culture system is 20 μM) for 4-5 hour treatment under the conditions of 37° C. and 5% $CO_2$, fixed with paraformaldehyde (1%), wash and re-suspend with penetration buffer, stain with anti-mouse IFN-γ-PE monoclonal antibody and anti-mice CD8 monoclonal antibody, wash twice with PBS, re-suspend with 500 μlPB, and load into flow cytometry for cell counting with the solution containing no peptide as control.

Repeat the test twice.

Tetramer staining results, shown in FIG. 2 (1 indicated naive T cells, 2 anti-influenza virus-specific T cells, 3 double-specific T cells). The results demonstrated that 10-15% double-specific T cells could response with MP tetramer, 15-20% with gp100 tetramer responses, but almost no response of anti-influenza virus-specific T cells in the control group with gp100 tetramer appeared, which indicated that the double-specific T-cell could express anti-melanoma antigens gp100 TCR as well as anti-influenza virus antigen MP-TCR, in this sense, it showed dual specificity.

In FIG. 2A, X-axis indicated the relative intensity of green fluorescence of the differentiation antigen-8 of 10-day dual specific T cells; while the Y-axis indicated the relative intensity of red fluorescence of the MP peptide tetramer (PE).

In FIG. 2B, X-axis indicated the relative intensity of green fluorescence of the differentiation antigen-8 of 10-day non-transduced T cells induced by influenza virus; while the Y-axis indicated the relative intensity of red fluorescence of the MP peptide tetramer (PE).

Figure 3:
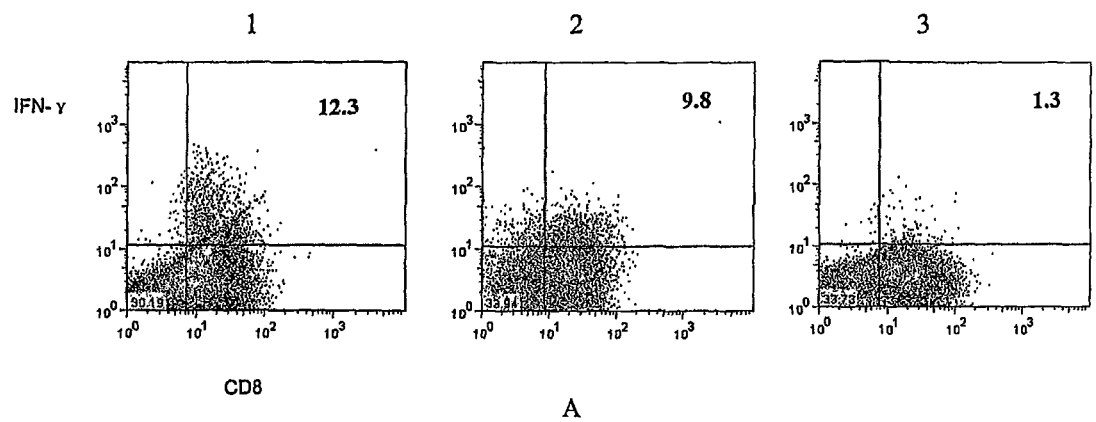
Figure 3:
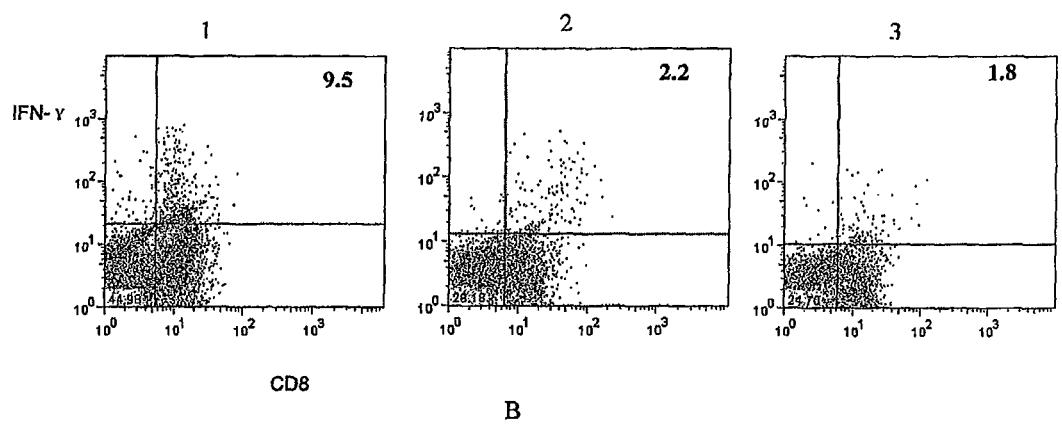

The staining results of intracellular cytokine were shown in FIG. 3, indicating about 10% double-specific T cells could response with influenza virus antigen and secrete γ-interferon, while about 10% could response with melanoma antigen gp100 peptide and secrete γ-interferon. It indicated the dual specificity of double-specific T-cells on the cytokine secretion levels.

FIGS. 3A and 3B demonstrated the staining results of intracellular cytokine of the double-specific T cells and anti-influenza virus-specific T cells, respectively, where 1 indicated the influenza virus antigen MP peptide response group, 2 the melanoma antigens gp100 peptide response group, and 3 the control group without peptide. X-axis indicated the relative intensity of green fluorescence of the differentiation antigen-8 of mice leukocyte, while Y-axis indicated the relative intensity of red fluorescence of the intraocular mice IFN-γ (PE).

2 Proliferation of Double-Specific T-Cell In Vitro or In Vivo of Mice

B16-AAD melanoma cells (Mullins, D. W., et al. Route of Immunization with Peptide-pulsed Dendritic Cells Controls the Distribution of Memory and Effector T Cells in Lymphoid Tissues and Determines the Pattern of Regional Tumor Control. J Exp Med, 2003.198 (7): p. 1023-24.)(IMCAS).

(A) In Vitro Proliferation:

After staining double-specific T-cells with green fluorescent dye (CFSE), different stimuli and IL-2 are added (the final concentrations of IL-2 at 50 IU/ml) (once every one day) to co-culture for 3 days under the conditions of 37° C. and 5% $CO_2$, and loaded into flow cytometry to observe cell proliferation.

Processed with different stimuli as follows:

1) Add influenza virus-feeder cells, and the ratio of feeder cells to double-specific T cells ratio is 1:1;

Preparation of Influenza viruses-feeder cells: take the HLA-A2/Kb transgenic mice spleen T cells without any immunization, inoculate them into co-culture medium, add influenza virus (with its final concentrations in the culture system up to $2 \times 10^6 EID_{50}$/ml) to stimulate for 2 h, then add mitomycin (with its final concentrations in the culture system up to 80 μg/ml), treated at 37° C. for 2 h, wash 3 times with medium, and the obtained cells are feeder cells combined with Influenza viruses.

2) Add B16-AAD melanoma cells processed with mitomycin, and the ratio of them to double-specific T cells is 0.5:1;

Preparation of B16-AAD melanoma cells treated with mitomycin: inoculate B16-AAD melanoma cells into co-culture medium, add mitomycin (with its final concentration in the culture system up to 200 μg/ml), treated at 37° C. for 2 h, wash 3 times with medium, and the obtained cells are B16-AAD melanoma cells processed with mitomycin.

3) Only double-specific T cells are cultivated in the co-culture medium, and no other cells are added.

4) Add anti-CD3 antibody up to the final concentrations of 200 ng/ml.

Repeat the test 3 times.

The in vitro proliferation results are shown in FIG. 4. After the co-culture with the feeder cells combined with influenza viruses, and anti-CD3 antibody, the double-specific T-cells showed significant proliferation, while B16-AAD melanoma cells could stimulate weakly proliferation of the abovementioned T cells, which indicated that the tumor antigen was a weak immunogen and could not effectively stimulate the proliferation of double-specific T cells, while the influenza virus antigen was a strong antigen and could strongly stimulate the above proliferations.

In FIG. 4, A indicates double-specific T cells while B anti-influenza virus-specific T cells. 1 represents the co-culture group with influenza virus-feeder cells, 2 the co-culture group with B16-AAD melanoma cells, 3 the blank culture group cultured in co-culture medium, and 4 the co-culture group with anti-CD3 antibody, respectively.

(B) In Vivo Proliferation of Mice

Transfuse double-specific T cells ($3 \times 10^6$/mouse) into mice intravenously, 24 h later, immunize mice with influenza virus (intraperitoneal immunization, once, $10^{7.9} EID_{50}$), detect gp100 tetramer and CD8 double positive cells in the mice spleen cells at different time points, observe the in vivo proliferation of T cells of mice after stimulation with influenza virus. Repeat the test twice.

The in vivo proliferation results are shown in FIG. 5. After immunized with influenza virus, the double-specific T cells (●) of mice demonstrated a significant in vivo proliferation. The anti-tumor TCR expression reached the highest 7 days after immunization, accounting for about 10% of CD8 positive T cells, afterwards the ratios decreased due to the response of in vivo immune balance system. It indicated that influenza virus antigen could effectively stimulate the in vivo proliferation of double-specific T cells, while no expression of anti-tumor TCR was detected in the controlled anti-influenza virus-specific T cells (○).

3 In Vivo and In Vitro Killing Test of Double-Specific T Cells

EG7cells (Fu, H. M., et al. Investigation of endogenous antigen processing by delivery of an intact protein into cells. J. Immunol. Methods, 2008.335: p. 90-97) (IMCAS).

K41cells (Fu, H. M., et al. Investigation of endogenous antigen processing) by delivery of an intact protein into cells. J. Immunol. Methods, 2008.335: p. 90-97) (IMCAS).

(A) In Vitro Killing:

Stain HLA-A2/Kb transgenic mice spleen cells with CFSE (10 μM), stimulate them with melanoma antigen gp100 peptide (10 μM, 37° C., 30 min), influenza virus antigen MP peptide (10 μM, 37° C., 30 min), and influenza virus (2EID50/cell, 37° C., 120 min) respectively, mix them with the effector cells (double-specific T cells) at different effector-target ratios for 4 h at 37° C., stain them with PI (propidium iodide, 10 μg/ml, Sigma-Aldrich, 81845), and load the prepared cells into flow cytometry for the measurement of killing ratio. Repeat the test 3 times.

The in vitro killing results are shown in FIG. 6. A indicates in vitro killing target cells combined with specific antigen of double-specific T cells, while B in vitro killing tumor cells of double-specific T cells.

In FIG. 6A, 1 indicates that target cells are the syngeneic mice spleen cells combined with gp100 peptide; 2 indicates that target cells are the syngeneic mice spleen cells combined with MP peptide; 3 indicates that target cells are the syngeneic mice spleen cells combined with influenza virus; 4 indicates that target cells are the syngeneic mice spleen cells receiving no stimulation. ● indicates that effector cells are double-specific T-cells. ○ indicates that effector cells are the syngeneic mice spleen cells without any antigen stimulation (control).

In FIG. 6B ● indicates the results of killing B16-AAD melanoma cells, ○ indicates the results of killing EG7 cells, and ■ indicates the result of killing K41 cells.

The results demonstrated that the double-specific T-cells could significantly kill the syngeneic mice spleen cells combined with gp100 peptide, MP peptide or influenza virus, but fail to kill the non-combined mice spleen cells (FIG. 6A). Furthermore, the double-specific T-cells could significantly kill the B16-AAD melanoma cells (FIG. 6B ●), but fail to kill the controlled tumor target cells ((FIG. 6B ○, ■).

(B) In Vivo Killing:

Transfuse $1 \times 10^7$ double-specific T-cells into HLA-A2/Kb transgenic mice intravenously, after 24 hours, immunize the mice with influenza virus (intraperitoneal immunization once, $10^{7.9}$ $EID_{50}$) Seven days later, transfuse target cells intravenously, and after 4 hours, the mice spleen cells were processed and added to the flow cytometry to observe the killing situations of the selected PKH26 positive cells. The target cells are prepared as follows: stain HLA-A2/Kb transgenic mice spleen cells with PKH26 (4 μM) and CFSE (2 μM, or 0.2 μM) respectively, stain strongly with CFSE (2 μM) the target cell groups combined with gp100 or influenza virus as test groups, and at the same time stain weakly with CFSE (0.2 μM) the target cell groups without stimuli as the control group. Mix the target cell groups stained strongly and weakly with CFSE at a ratio of 1:1 ($2.5 \times 10^6$ cells/group) and transfuse them into the test mice intravenously as target cells. Repeat the test 3 times.

The in vivo killing results are shown in FIG. 7, where 1 is the control group, indicating the in vivo killing test results seven days after the injection of PBS in mice; 2 represents the test groups, indicating the in vivo killing test results seven days after the injection of double-specific T cells (2A and 2B) or influenza virus-specific T cells (2C) in mice respectively, and immunization with influenza virus after 24 hours.

A and C indicate killing the target cells combined with gp 100 tumor antigen, while B indicates killing the target cells combined with influenza virus.

The results indicated that the double-specific T cells could kill the target cells combined with gp 100 tumor antigen (FIG. 7A) with the mean killing rate up to 65%, and kill the target cells combined with influenza virus (FIG. 7B) with the mean killing rate up to 48.5%, however, by comparison, the influenza virus-specific T cells could not kill the target cells combined with gp 100 tumor antigen (FIG. 7C)

4 The in vivo inhibiting tumor test of nude mice of the double-specific T cells

Balb/c nu/nu nude mice: purchased from Peking University Health Science Laboratory Animal Research Center.

Inoculate $8 \times 10^4$ B616-AAD mice melanoma cells into Balb/c nu/nu nude mice subcutaneously, after 24 hours, inject $1 \times 10^6$ double-specific T cells intravenously, at the same time inject anti-influenza virus-specific T cells as the control group. After another 24 hours, stimulate T-cell proliferation with intraperitoneal immunization of influenza virus ($10^{7.9}$ $EID_{50}$. afterwards immunization once every 7-10 days). Observe the in vivo tumor growth of nude mice. The tumor volume $(cm^3)$=long tumor diameter (cm)×[short tumor diameter $(cm)]^2/2$.

The results are shown in FIG. 8. The double-specific T cells (FIG. ■, n=10) could significantly inhibit in vivo proliferation of melanoma cells of nude mice. Compared with that in control group (no injection of T cells ● (n=7)) and anti-influenza virus-specific T Cell injection group ○ (n=7), the tumor volume in double-specific T cells injection group indicated significant differences (p<0.05).

INDUSTRIAL APPLICATION

The invention method to obtained the anti bi-specific T cells with transferring the recognition target antigen B p-MHC immune recognition molecules. Primary use the specificity of its anti-immunogen A, induced by immunogen A to proliferate overcome the weak immunogenicity of the past can not induce antigen-specific T cell proliferation defects in vitro, amplification effect, amplified by the immune cells of the target antigen destruction rate; in addition, the proliferation of) methods of the present invention is simple, cost low. Therefore, Methods of the present invention can be applied to greatly produce various kinds of target antigen-specific immune cells, which will be used for immune infusion therapy of diseases such as multitypes of tumors and so on.

The invention claimed is:

1. A method for expanding bi-specific T cells, comprising:
   (1) stimulating T cells with antigen A to generate T cells specific to a peptide-MHC complex of antigen A,
   (2) transferring a gene encoding an immune recognition molecule for targeting a peptide-MHC complex of antigen B into the T-cells specific to the peptide-MHC complex of antigen A to obtain bi-specific T-cells that are specific to both antigen A and antigen B, and
   (3) stimulating the bi-specific T-cells with antigen A, thereby expanding the bi-specific T-cells,
   wherein antigen A is a virus, bacterium, amino acid peptide, chimeric protein, or allogeneic antigen with more than 7 and less than 35 amino acids,
   wherein the immune recognition molecule for targeting a peptide-MHC complex of antigen B is melanoma differentiation antigen gp100-specific T cell receptor (TCR), and
   wherein the gene encoding melanoma differentiation antigen gp 100-specific TCR comprises SEQ ID NO: 1 encoding the TCR α subunit and SEQ ID NO:2 encoding the TCR β subunit.

2. The method of claim 1, wherein step (3) is performed in vitro or/and in vivo.

3. The method of claim 1, wherein step (3) is performed by:
   (a) transfusing antigen B-specific T-cells into a living object immunized with antigen A,
   (b) culturing antigen B-specific T-cells in the presence of antigen A, or
   (c) co-culturing antigen B-specific T-cells and feeder cells in the presence of antigen A.

4. The method of claim 1, wherein step (2) is performed using a viral vector, liposome, cationic polymer, or electroporation.

5. The method of claim 4, wherein the viral vector is a retroviral vector, lentiviral vector, or adeno-associated viral vector.

6. The method of claim 4, wherein step (2) is performed by:
   (a) co-culturing recombinant virus packaging cells and antigen A-specific T-cells in the presence of antigen A or its derived peptide,
   (b) co-culturing recombinant virus packaging cells, antigen A-specific T-cells, and feeder cells expressing antigen A or pulsed with antigen A-derived peptide;
   (c) co-culturing recombinant virus and antigen A-specific T-cells in the presence of antigen A or antigen A-derived peptide; or
   (d) co-culturing recombinant virus, antigen A-specific T-cells, and feeder cells expressing antigen A or pulsed with antigen A-derived peptide;
   wherein the recombinant virus comprises a gene encoding an immune recognition molecule that recognizes antigen B peptide-MHC complex.

7. The method of claim 1, wherein the virus is influenza virus, EB virus, or CMV virus.

8. The method of claim 1, wherein the T-cells specific to the peptide-MHC complex of antigen A are generated by immunizing animals with antigen A.

9. The method of claim 1, wherein the gene encoding the immune recognition molecule is transferred by (a) viral vectors selected from the group consisting of retroviral vectors, lentiviral vectors and adeno-associated virus vectors, (b) liposomes, (c) cationic polymers, or (d) electroporation.

10. The method of claim 1, wherein the gene encoding the immune recognition molecule is transferred by:
   a. co-culturing packaging cells that produce recombinant virus with antigen A-specific T cells and antigen A;
   b. co-culturing packaging cells that package recombinant virus with antigen A-specific T cells and feeder cells expressing MHC associated with a peptide of antigen A;
   c. co-culturing recombinant virus, antigen A-specific T cells, and antigen A; or
   d. co-culturing recombinant virus, antigen A-specific T cells, and feeder cells expressing MHC associated a peptide from antigen A;
   wherein the recombinant virus contains the gene encoding an immune recognition molecules for targeting a peptide-MHC complex of antigen B.

* * * * *